US010576647B2

(12) United States Patent
Uit De Bulten et al.

(10) Patent No.: US 10,576,647 B2
(45) Date of Patent: Mar. 3, 2020

(54) SYSTEM AND A METHOD FOR TREATING A PART OF A BODY

(71) Applicant: KONINKLIJKE PHILIPS N.V., Eindhoven (NL)

(72) Inventors: Raymon Henk Uit De Bulten, Eindhoven (NL); Pascal Homan, Eindhoven (NL); Everhardus Johannes Hoexum, Eindhoven (NL); Arjan Sander Vonk, Eindhoven (NL); Luc Berntsen, Eindhoven (NL); Eduard Matheus Johannes Niessen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 75 days.

(21) Appl. No.: 15/032,126

(22) PCT Filed: Oct. 24, 2014

(86) PCT No.: PCT/EP2014/072848
§ 371 (c)(1),
(2) Date: Apr. 26, 2016

(87) PCT Pub. No.: WO2015/067484
PCT Pub. Date: May 14, 2015

(65) Prior Publication Data
US 2016/0297085 A1 Oct. 13, 2016

(30) Foreign Application Priority Data
Nov. 6, 2013 (EP) ...................................... 13191740

(51) Int. Cl.
B26B 19/38 (2006.01)
B26B 21/40 (2006.01)
(Continued)

(52) U.S. Cl.
CPC ............ *B26B 19/388* (2013.01); *A45D 26/00* (2013.01); *A45D 44/02* (2013.01); *A61B 17/54* (2013.01);
(Continued)

(58) Field of Classification Search
CPC ... B26B 19/388; B26B 19/20; B26B 21/4056; B26B 21/4081; A45D 26/00; A45D 44/02; A61B 17/54; A61N 5/0617
(Continued)

(56) References Cited
U.S. PATENT DOCUMENTS 2,765,796 A 10/1956 Guenther
2,972,351 A 2/1961 Morgan
(Continued)

FOREIGN PATENT DOCUMENTS

DE 102010023681 12/2011
WO 2004033164 4/2004
(Continued)

*Primary Examiner* — Ghassem Alie
*Assistant Examiner* — Nhat Chieu Q Do

(57) ABSTRACT

The present application relates to a system for treating a part of a body to be treated. In particular, the present invention relates to a system for cutting hair on a part of a body to be treated. The system has a hand-held treating device having a treating unit. The system also has an imaging module configured to generate information indicative of the position of the treating device relative to the part of the body to be treated based on an image of a part of the body and the treating device. A controller is configured to change an operating characteristic of the treating device in dependence on the information generated by the imaging module. The present application also relates to a treating device configured to be used in a system as described above and a method for treating a part of a body to be treated.

15 Claims, 3 Drawing Sheets

(51) Int. Cl.
  *A45D 26/00* (2006.01)
  *A45D 44/02* (2006.01)
  *A61B 17/54* (2006.01)
  *A61N 5/06* (2006.01)
  *B26B 19/20* (2006.01)
  *A45D 44/00* (2006.01)
  *A61N 5/067* (2006.01)

(52) U.S. Cl.
  CPC ............ *A61N 5/0617* (2013.01); *B26B 19/20* (2013.01); *B26B 19/38* (2013.01); *B26B 21/4056* (2013.01); *B26B 21/4081* (2013.01); *A45D 2026/008* (2013.01); *A45D 2044/007* (2013.01); *A61N 2005/067* (2013.01)

(58) Field of Classification Search
  USPC ...................................... 83/76.2; 30/200–201
  See application file for complete search history.

(56) References Cited

U.S. PATENT DOCUMENTS

| | | | |
|---|---|---|---|
| 3,060,574 A * | 10/1962 | Thomas | B26B 19/20 30/202 |
| 3,241,562 A | 3/1966 | Gronier | |
| 3,413,985 A | 12/1968 | Dlouhy | |
| 4,602,542 A | 7/1986 | Natrasevschi | |
| 6,279,234 B1 * | 8/2001 | Chaouachi | B26B 19/20 30/200 |
| 7,282,060 B2 | 10/2007 | DeBenedictis | |
| 7,992,307 B2 * | 8/2011 | Smal | B26B 19/20 30/202 |
| 8,341,846 B1 * | 1/2013 | Holmes | B26B 19/205 30/200 |
| 8,667,692 B2 | 3/2014 | Kraus | |
| 9,375,281 B2 | 6/2016 | Moench | |
| 2005/0127058 A1 | 6/2005 | Shalev | |
| 2012/0233866 A1 * | 9/2012 | Kammer | B26B 19/3853 30/201 |
| 2015/0197016 A1 * | 7/2015 | Krenik | B26B 19/3806 83/13 |
| 2015/0321365 A1 | 11/2015 | Lauritsen | |

FOREIGN PATENT DOCUMENTS

| | | |
|---|---|---|
| WO | 2013011380 A2 | 1/2013 |
| WO | 2013011505 | 1/2013 |
| WO | 2013096572 A1 | 6/2013 |

* cited by examiner

SYSTEM AND A METHOD FOR TREATING A PART OF A BODY

FIELD OF THE INVENTION

The present invention relates to a system for treating a part of a body to be treated. In particular, the present invention relates to a system for cutting hair on a part of a body to be treated. The present invention also relates to a treating device configured to be used in a system as described above and a method for treating a part of a body to be treated.

BACKGROUND OF THE INVENTION

Devices for treating a part of a body, for example by cutting hair on a part of a body to be treated, include powered hand-held devices that are placed against a part of a user's body and moved over areas where hair is to be cut, for example a trimmer. Such devices include mechanical hair cutting devices. The user selects a cutting length by adjusting or selecting a guide, such as a comb, which extends over a cutting blade and then selects which areas of hair to cut and which areas should not be cut by positioning and moving the device appropriately.

When cutting a user's own hair, or someone else's hair, significant skill is required to create a particular hairstyle or to provide a presentable result. Furthermore, it is difficult to repeat the haircut, or to copy a haircut. Although it is possible to use a trimmer to cut hair, such a device generally provides for cutting hair to a consistent length across the head. Such devices are difficult to accurately position on a user's head, for example. The accuracy of the treatment provided by the device depends on the user's skill and steady hand. Moreover, the device and the user's hand and arm may impede the user's view thereby making it difficult to position and move the device accurately.

SUMMARY OF THE INVENTION

It is an object of the invention to provide a system and/or a method for treating a part of a body to be treated which substantially alleviates or overcomes the problems mentioned above.

According to the present invention, there is provided a system for treating a part of a body to be treated comprising a hand-held treating device having a treating unit, a position identifier configured to generate information indicative of the position of the treating device relative to the part of the body to be treated, and a controller configured to adjust an operating characteristic of the treating device in dependence on the information generated by the position identifier.

Therefore, the system is operable to determine the position of the treating device based on information generated by the position identifier. This minimises the number of components that are required. With such an arrangement it is possible to change an operating characteristic of the treating device to aid performance of the treating device when the treating device is used on a part of a body to be treated, for example by cutting hair. This enables an operating condition of the treating device to be changed based on information generated by the position identifier.

The system for treating a part of a body to be treated is a system for cutting hair on a part of a body to be treated, the treating device is a cutting device, and the treating unit is a cutting unit.

With such an arrangement, it is possible to provide a system for cutting hair which provides for different hairstyles to be produced by changing an operating characteristic of the treating device in dependence on the information generated by the position identifier. Therefore, it is possible to automatically and dynamically adjust the characteristic as the position of the treating device relative to the part of the body to be treated, for example a user's head, changes.

The operating characteristic of the treating device may be adjustable in response to user input, the controller may be configured to determine one or more adjustments of the operating characteristic made in response to user input, and the controller may be configured to form a profile of the part of the body to be treated based on the one or more adjustments of the operating characteristic made in response to user input determined by the controller together with the information indicative of the position of the treating device relative to the part of the body to be treated.

With the above arrangement it is possible for the controller to form a profile of one or more operating characteristic conditions for one or more positions of the treating device relative to the part of the body to be treated as determined by the position identifier. This therefore enables a set of conditions of the operating characteristic to be repeated, and such a profile to be stored to be used by the controller to adjust the operating characteristic to a desired condition for a given position without manual adjustment by a user. The controller is able to dynamically adjust the operating characteristic based on the profile formed by the controller.

The controller may be configured to refer to a reference profile of the part of the body to be treated to determine the adjustment of the operating characteristic in dependence on the position of the treating device relative to the part of the body to be treated, and the controller may be configured to modify the reference profile of the part of the body to be treated in response to a user input determined by the controller to form a new reference profile.

With such an arrangement it is possible for a user to change an existing profile based on one or more desired conditions of the operating characteristic to form a new profile. The new profile may replace or be stored together with the existing profile. Therefore a user is able to With such an arrangement the user input may be configured to make an adjustment of the operating characteristic which is determined by the controller to modify the reference profile. In one alternative arrangement, the user input is determined by the controller and used to modify the reference profile without the user input making a direct adjustment to the operating characteristic.

The controller may be configured to form the reference profile based on a user input determined by the controller together with the information indicative of the position of the treating device relative to the part of the body to be treated.

An advantage of this arrangement is that it is relatively straightforward to form a reference profile which may then be referred to by the controller to adjust the operating characteristic in dependence on the information indicative of the position of the treating device relative to the part of the body to be treated.

The controller may be configured to adjust the operating characteristic of the treating device in dependence on a reference profile of the part of the body to be treated, the operating characteristic of the treating device may be adjustable in response to user input, and the controller may be configured to determine one or more adjustments of the operating characteristic made in response to user input, wherein the controller may be configured to modify the reference profile of the part of the body to be treated based on the one or more adjustments of the operating characteristic made in response to user input determined by the controller together with the information indicative of the position of the treating device relative to the part of the body to be treated.

With this arrangement it is possible to easily adjust the operating characteristic during use of the treating device and to use this adjustment during future use of the system. Such an arrangement provides for manual adjustment of the operating characteristic to be recorded. This means that use of the system may be personalised, and treatment provided by the system may be improved.

The controller may be configured to form the reference profile based on the one or more adjustments of the operating characteristic made in response to user input together with the information indicative of the position of the treating device relative to the part of the body to be treated.

The profile of the part of the body to be treated may comprise a map of one or more conditions of the operating characteristic together with information indicative of the position of the treating device relative to the part of the body to be treated.

Therefore, it is relatively straightforward to store the desired operating condition for a given position of the treating device relative to the part of the body to be treated.

The controller may be configured to change an operating characteristic of the treating device in dependence on the information generated by the position identifier is configured to change two or more operating characteristics of the treating device in dependence on the information generated by the position identifier.

With such an embodiment it is possible to maximise the effectiveness and/or efficiency of the treatment provided by the system. For example, with the treating device being a cutting device, in one embodiment it is possible to dynamically change the cutting height, and therefore the cut length of hair, and also to change another operating condition, such as a handling characteristic of the cutting device to improve comfort to a user, in dependence of the information indicative of the position of the treating device relative to the part of the body to be treated. Therefore, it is possible to improve the experience to a user during the forming of a desired hairstyle.

The or one of the operating characteristics of the treating device that the controller is configured to adjust is an operating characteristic of the treating unit.

With such an arrangement it is possible to change an operating characteristic of the treating unit to alter the treatment applied to the part of the skin to be treated.

The system may further comprise a driver configured to drive the treating unit, the controller being configured to determine the rate at which the treating device is moved relative to the part of the body to be treated in dependence on the information generated by the position identifier, and wherein the or one of the operating characteristics of the treating unit that the controller is configured to adjust is operation of the driver in dependence on the determined rate at which the treating device is moved relative to the part of the body to be treated.

This means that it is possible to change the rate and/or mode of operation of the treating unit in dependence of the position of the treating unit relative to the part of the body to be treated.

The treating unit may further comprise a stationary treating element and a moveable treating element, the moveable treating element may be adjustable relative to the stationary treating element, and the or one of the operating characteristics of the treating device that the controller is configured to adjust may be the position of the moveable treating element relative to the stationary treating element.

With such an arrangement it is possible to change an operating characteristic of the treating unit to alter the treatment applied to the part of the skin to be treated.

The stationary treating element may be a stationary blade with a stationary blade edge and the moveable treating element may be a moveable blade with a moveable blade edge arranged parallel to the stationary blade edge which is moveable in a reciprocal manner against the stationary blade in a hair shearing engagement, wherein the stationary blade and the moveable blade may be moveable relative to each other in a direction perpendicular to the reciprocating motion of the moveable blade to vary the distance between the stationary blade edge and the moveable blade edge, and the or one of the operating characteristics of the treating unit that the controller is configured to adjust may be the distance between the stationary blade edge and the moveable blade edge.

This means that it is possible to adjust the cutting ability of the treating unit. Therefore, it may be possible to adjust the cutting length independent of any movement of a guide. This arrangement may help provide a more skin-friendly device by reducing irritation.

The treating device may further comprise a guide having a guide face configured to space the treating unit from the part of the body to be treated during use of the system.

The or one of the operating characteristics of the treating unit that the controller is configured to adjust may be the distance between the treating unit and the guide face.

The guide may be configured to be moveable about the treating unit to follow the contours of the part of the body to be treated, and the or one of the operating characteristics of the treating unit that the controller is configured to adjust may be the extent of allowable movement of the guide about the treating unit.

Therefore, it is possible to manipulate the allowable movement of the guide based on the indicated position of the treating device relative to the part of the body to be treated. This means that it is possible to help improve comfort of the user by varying the allowable movement of the guide on different areas of the part of the body to be treated. For example, on a delicate area of the part of the body to be treated the guide may be configured to be movable to allow for a gentle movement over the area, whereas on a tougher area the guide may be configured to be rigid to allow for an increased rate of movement.

The or one of the operating characteristics of the treating unit that the controller is configured to adjust is the angular position of the guide.

Therefore, it is possible to manipulate the angular position of the guide based on the indicated position of the treating device relative to the part of the body to be treated. This means that it is possible to help improve comfort of the user by varying the angular position of the guide on different areas of the part of the body to be treated.

The guide may comprise comb teeth defining a leading edge of the guide, and the comb teeth may be extendable from one end of the treating unit. The or one of the operating characteristics of the treating unit that the controller is configured to adjust may be the extent to which the comb teeth extend from the one end of the treating unit.

An advantage of this arrangement is that it allows the precision at which the treatment is applied to be varied. For example, when the comb teeth are retracted the precision is increased to allow a more accurate treatment for a given cutting height of the guide due to the distance between the leading edge of the guide and the cutting unit being reduced. Whereas, by extending the comb teeth an increased hair lifting effect is produced for a given cutting height of the guide which helps to maximise the performance of the cutting device.

The or one of the operating characteristics of the treating device that the controller is configured to adjust may be the shape of the treating device. The treating device may further comprise a main body, and the or one of the operating characteristics of the treating device that the controller is configured to adjust is the shape of the main body.

With such an arrangement the handling of the treating device may be maximised. Furthermore, it may be possible for the shape of the treating device to be manipulated to maximise visibility of the part of the body to be treated.

The position identifier configured to generate information indicative of the position of the treating device relative to the part of the body to be treated may comprise an imaging module configured to generate information indicative of the position of the treating device relative to the part of the body to be treated based on an image of a part of the body and the treating device.

Therefore, the system is operable to determine the position of the treating device based on an image of a part of the body and the treating device. This minimises the number of components that are required.

The image of a part of the body and the treating device may be an image of the part of the body to be treated and the treating device.

Therefore, the accuracy of the system may be maximised due to the image being an image of the part to be treated. Furthermore, the arrangement of the system is simplified because the imaging module is able to provide direct information about the part of the body to be treated.

The image of a part of the body and the treating device may be an image of a user's head and the treating device, wherein the imaging module may be configured to detect a gaze direction of the user's head based on the image of the user's head and the treating device.

The imaging module may be configured to detect the gaze direction of the user's head based on detection of one or more objects in the image of the user's head and the treating device and, optionally, based on detection of the user's nose and/or ears in the image of the user's head and the treating device.

With this arrangement the imaging module is capable of accurately providing information indicative of the position of the treating device relative to the user's head by detecting one or more easily identifiable objects, such as features of the head. Furthermore, by detecting the user's nose and/or ears in the image of the user's head it is possible to easily identify the gaze direction and/or determine the location of other parts of the user's head due to the user's nose and/or ears being in a fixed location relative to other parts of the user's head. It will also be recognised that the user's nose and/or ears are easily determinable by an imaging module due to the objects protruding from the remainder of the head. Although the user's nose and/or ears are easily determinable by an imaging module, it will also be recognised that the position of other features may be determined, for example a user's eyes and/or mouth due to their contrast with the remainder of the user's face.

The position identifier configured to generate information indicative of position of the treating device relative to the part of the body to be treated may comprise an electromagnetic field detector configured detect changes in an electromagnetic field to generate information indicative of the position of the treating device relative to the part of the body to be treated based on a detected electromagnetic field.

With this arrangement it is possible to provide a straightforward means of generating information indicative of position of the treating device relative to the part of the body to be treated.

According to another aspect of the invention, there is provided a treating device configured to be used in the system as described above.

According to another aspect of the present invention, there is provided a method of treating a part of a body to be treated using a treating device comprising generating information indicative of the position of the treating device relative to the part of the body to be treated using a position identifier, adjusting an operating characteristic of the treating device in dependence on the information generated by the position identifier, adjusting the operating characteristic of the treating device in response to user input, determining the one or more adjustments of the operating characteristic in response to user input, and forming a profile of the part of the body to be treated based on the determined one or more adjustments of the operating characteristic in response to user input together with the information indicative of the position of the treating device relative to the part of the body to be treated.

According to another aspect of the present invention, there is provided a method of treating a part of a body to be treated using a treating device comprising generating information indicative of the position of the treating device relative to the part of the body to be treated based on an image of a part of the body and the treating device using a position identifier, and adjusting two or more operating characteristics of the treating device in dependence on the information generated by the position identifier.

With such a method, the treating device may comprise a treating unit and a guide face configured to space the treating unit from the part of the body to be treated during use of the system, and one of the two or more operating characteristics of the treating unit that is adjustable in dependence on the information generated by the position identifier may be the distance between the treating unit and the guide face.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
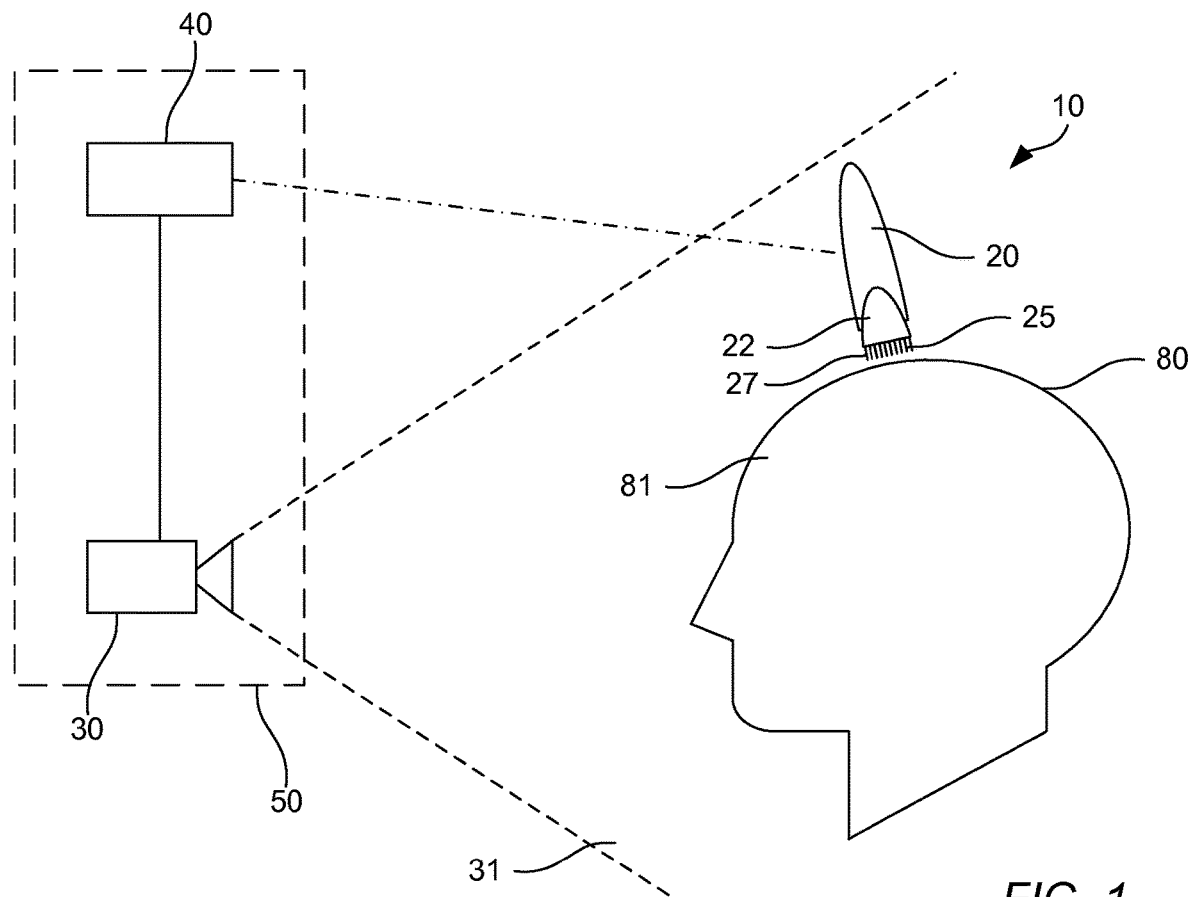
FIG. 1 shows a schematic view of a system for cutting hair.

Embodiments described herein describe a system for cutting hair. Referring to FIG. 1, a system for cutting hair 10 is shown. The system for cutting hair 10 acts as a system for treating part of a body to be treated. The system 10 comprises a cutting device 20, and a camera 30. The camera 30 acts as an imaging module. The camera 30, acting as an imaging module, is a position identifier configured to generate information indicative of the position of the treating device relative to the part of the body to be treated. That is, a position identifier is capable of generating information indicative of the position of one or more elements. The system 10 further comprises a controller 40. The controller 40 is configured to operate the cutting device 20.

Although in the present described embodiments the position identifier is an imaging module, it will be understood that alternative means or complimentary means of generating information indicative of the position of one or more elements, in particular a part of a body to be treated and a cutting device, may be used. Examples of such a position identifier include electromagnetic field detection, microwave detection, inertial measurement, and/or ultrasonic detection. An example of a system using electromagnetic field detection to generate information indicative of the position of the treating device relative to the part of the body to be treated is known from WO2013/096572.

In the embodiments described herein, the system 10 is described by reference to the user of the system 10 being the person being treated. That is, the user is using the system to treat themselves. However, it will be understood that in an alternative embodiment the user is a person using the system 10 to apply treatment using the system 10 to another person.

The camera 30 and controller 40 form part of a base unit 50. Alternatively, the camera 30 and controller 40 are disposed separately. In one embodiment, the controller 40 is in the cutting device 20. The camera 30, controller 40 and cutting device 20 communicate with each other. In the present embodiment the camera 30 and controller 40 communicate via a wired connection. The controller 40 and the cutting device 20 communicate via a wireless connection. Alternative arrangements are envisaged. For example, the controller 40 and cutting device 20 may be connected by a wired connection, and/or the controller 40 and the camera 30 may be connected by a wireless connection. Wireless modules, for example radio or infra-red transmitters and receivers, act to wirelessly connect the different components.

The base unit 50 in the present embodiment is a dedicated part of the system 10. However, it will be understood that the base unit 50 may be a device having an imaging module and a controller, amongst other components. For example, the base unit 50 may be or comprise a mobile phone, tablet computer or laptop computer, another mobile device, or a non-mobile device such as a computer monitor with an in-built or attached camera.

Figure 2:
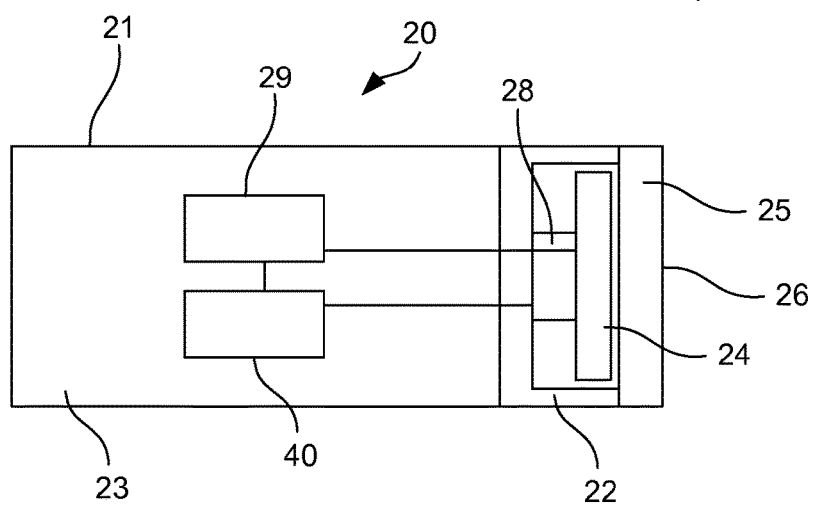
FIG. 2 shows a schematic view of a cutting device.

Referring to FIGS. 1 and 2, the cutting device 20 is a hand-held electrical hair trimming device. However, it will be apparent that the cutting device 20 may have an alternative arrangement. For example, the cutting device 20 may be a hand-held electrical shaving device. The cutting device 20 acts as a treating device. The cutting device 20 is moved over a skin 80 of a part of a user's body, for example their head 81, to trim hair on that part of the body. The cutting device 20 comprises a main body 21 and a cutting head 22 at one end of the main body 21. The main body 21 defines a handle portion 23. The body 21 and the cutting head 22 are arranged so that the handle portion 23 is able to be held by a user.

Figure 4:
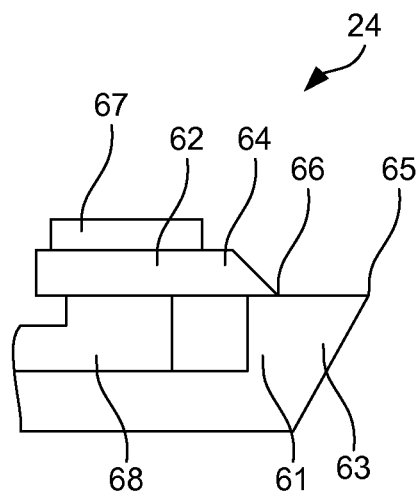
FIG. 4 shows a schematic partial cut-away side view of a cutting unit of an embodiment of the cutting device shown in FIG. 2 in a retracted condition.

The cutting head 22 has a cutting unit 24. The cutting unit 24 is configured to trim hair. The cutting unit 24 acts as a treating unit. Referring to FIG. 4, the cutting unit 24 has a stationary treating element 61, and a moveable treating element 62 which moves relative to the stationary treating element. Hairs protrude past the stationary treating element 61, and are cut by the moveable treating element 63. In particular, in one embodiment the stationary treating element 61 comprises a stationary blade 63, and the moveable treating element 62 comprises a moveable blade 64. The stationary blade 63 has a stationary edge 65 comprising a first array of teeth (not shown in FIG. 4 or 5). The moveable blade 64 has a moveable edge 66 comprising a second array of teeth (not shown in FIG. 4 or 5). The stationary edge 65 and moveable edge 66 are aligned parallel to each other. The moveable blade 64 is moveable in a reciprocal manner against the stationary blade 63 in a hair shearing engagement. Therefore, the second array of teeth is arranged to move in a reciprocal motion relative to the first array of teeth. In the present embodiment, the stationary treating element 61 and the moveable treating element 62 form cooperating mechanical cutting parts.

Although one cutting unit is described above, it will be understood that the cutting head 22 may comprise two or more cutting units. Although in the present arrangement the cutting unit comprises the stationary treating element 61 and the moveable treating element 62, it will be understood that alternative cutting arrangements are envisaged. For example, the cutting unit 24 may comprise a foil (not shown) through which hairs protrude, and a moving blade (not shown) which moves over the foil.

The cutting unit 24 is driven by a driver 29. The driver 29 acts to drive the cutting unit 24 in a driving action. In the present embodiment, the driver 29 is an electric motor. The driver 29 drives the moveable element relative to the stationary element in a reciprocal motion. The driver 29 is controlled by the controller 40.

The cutting head 22 has a guide 25. The guide 25 has a guide face 26. The guide face 26 forms an end surface. The guide face 26 is configured to be disposed against the part of the body to be treated. The guide face 26 is spaced from the cutting unit 24. However, in one embodiment the cutting head 22 may be adjustable so that the guide face 26 and the cutting unit 24 lie planar with each other. The guide face 26 is arranged to space the cutting head 22 from the part of the body to be trimmed, for example the skin 80 of a user's head 81. In another embodiment the guide 25 may be omitted.

In the present embodiment, the guide 25 is a comb. The guide 25 has a plurality of parallel, but spaced, comb teeth 27. The spaced comb teeth 27 allow the passage of hair therebetween to be exposed to the cutting unit 24 to be cut by the cutting unit 24. A distal surface of each tooth from the main body 21 forms the guide face 26. The guide 25 is mounted to the main body 21. The guide 25 is removably mounted to the main body 21. This enables the cutting unit 24 to be cleaned, and the guide 25 to be interchangeable with another guide and/or replaced.

The guide 25 has a leading edge 70. The leading edge 70 is aligned with the moveable edge 66 of the moveable blade 64, but is spaced therefrom. The leading edge 70 forms an edge of the guide face 26. The leading edge 70 is defined by ends of the comb teeth 27. The leading edge 70 defines an intersection between the guide face 26 of the guide 25 and a front face 71 of the guide 25.

The distance between the guide face 26 and the cutting unit 24 is adjustable. That is, the guide face 26 and the cutting unit 24 are moveable towards and away from each other. In the present embodiment the guide 25 is fixedly mounted to the main body 21. That is, the guide 25 is prevented from moving towards or away from the main body 21. However, the guide 25 may pivot about the main body 21. The cutting unit 24 is movably mounted to the main body 21. That is, the cutting unit 24 is movable towards and away from the guide face 26. The cutting unit 24 may also be pivotable relative to the main body 21. A distance actuator 28 acts on the cutting unit 24. The distance actuator 28 extends in the cutting head 22. The distance actuator 28 is operable to move the cutting unit 24 relative to the guide face 26.

The cutting unit 24 of this embodiment is mounted on the distance actuator 28 which is configured to move the cutting unit 24 in a linear direction towards and away from the skin contacting guide face 26, and therefore the skin 80 of the user during use. The distance actuator 28 is a linear actuator, and may be a mechanical actuator or an electro-magnetic actuator, for example. The distance actuator 28 moves the cutting unit 24 in response to commands from the controller 40.

Depending on the type of actuator used, the cutting unit 24 may be mounted on a linear sliding guide or rail such that the cutting unit 24 moves, under influence of the distance actuator 28, and remains parallel to the guide face 26. The movement may be in direction which is perpendicular to the guide face 26 or it may be at an angle.

With the above arrangement the cutting unit 24 moves relative to the guide face 26. Therefore, the guide face 26 is maintained in a stationary position with respect to the main body 21. This means that the distance between the guide face 26 and the handle 23 does not change during use of the cutting device 20. Therefore, there is no perceived movement of the cutting device 20 in a user's hand.

The distance between the cutting unit 24 and the guide face 26 is variable such that the cutting device 20 is at or between a minimum condition, in which the distance between the cutting unit 24 and the guide face 26 is at a minimum value, and a maximum condition, in which the distance between the cutting unit 24 and the guide face 26 is at a maximum value.

The cutting device 20 of the present embodiment is configured to have a maximum condition of about 100 mm. However, it will be understood that alternative ranges are possible. For example, a shaver for trimming facial hair may be configured to set a maximum condition of 10 mm. Such a reduced range may increase the accuracy of the cutting device 20.

Although in the above described embodiment the cutting unit 24 is movable relative to the guide face 26, in an alternative embodiment the guide 25, and therefore the guide face 26, is movable relative to the cutting unit 24. The cutting unit 24 may be fixedly mounted to the main body 21, and the guide 25 may be movable relative to the main body 21. In such an embodiment, the distance actuator acts on the guide 25. The guide face 26 is movable towards and away from the cutting unit 24. The guide 25 may be slideable on one or more rails to slide relative to the cutting unit 24. With such an embodiment, the arrangement of the cutting unit 24 is simplified.

In the above described arrangement the distance between the guide face 26 and the cutting unit 24 is adjustable by means of operation of the distance actuator. However, in one embodiment the distance between the guide face 26 and the cutting unit 24 is also manually adjustable by a user.

Although different arrangements for adjusting the distance between the guide face 26 and the cutting unit 24 are given above, it will be understood that in an alternative embodiment the distance between the guide face 26 and the cutting unit 24 is not adjustable. The guide face 26 and the cutting unit 24 may be fixedly mounted to each other. In one embodiment the guide may be removable and the system 10 may include two or more interchangeable guides which have different arrangements, for example to provide different distances between the guide face 26 and the cutting unit 24. In such arrangements the system 10 may be usable with the guide 25 removed from the remainder of the cutting device 20.

The camera 30, acting as an imaging module, is a depth or range camera. That is, the camera 30 uses range imaging to determine the position of elements within the field-of-view, or optical sensing zone 31, of the camera 30.

The camera 30 produces a two-dimensional image with a value for the distance of elements within the optical sensing zone 31 from a specific position, such as the camera sensor itself. In the present embodiment the camera 30 is configured to employ a structured light technique to determine the position, including the distance, of elements within the optical sensing zone 31 of the camera 30. Such a technique illuminates the field of view with a specially designed light pattern. An advantage of this embodiment is that the depth may be determined at any given time using only a single image of the reflected light. Alternatively, the camera 30 is configured to employ a time-of-flight technique to determine the position, including the distance, of elements within the field of view of the camera 30. An advantage of this embodiment is that the number of moving parts is minimised. Other techniques include echographic technologies, stereo triangulation, sheet of light triangulation, interferometry, and coded aperture.

The camera 30 is a digital camera capable of generating image data representing a scene received by the camera's sensor. The image data can be used to capture a succession of frames as video data. The optical sensing zone 31 is the field-of-view within which optical waves reflecting from or emitted by objects are detected by the camera's sensors. The camera 30 detects light in the visible part of the spectrum, but can also be an infra-red camera.

The camera 30, acting as the imaging module, is configured to generate information indicative of the position of elements within the optical sensing zone 31. The camera 30 generates the information based on the image data generated by the camera's sensor.

In the present embodiment, the camera 30, acting as the imaging module, generates a visual image with depth, for example an RGB-D map. The camera 30 generates a visual image with depth map of the elements within the optical sensing zone 31 of the camera 30. Alternative means of generating information indicative of the position of elements within the optical sensing zone 31 are anticipated. For example, the camera 30 may generate a depth image (D-map) of the elements within the optical sensing zone 31.

The camera 30 is configured to generate a visual image with depth map with 30 frames per minute. Furthermore, the camera 30 has a resolution of 640×480. The depth range is between 0.4 m and 1.5 m. The angle of the field-of-view is between 40 degrees and 50 degrees. This provides a suitable area for a user to be positioned within the optical sensing zone 21. The depth resolution is configured to be about 1.5 mm within the optical sensing zone 21.

Whilst the above parameters have been found to be sufficient for accurate determination of position for cutting hair, it will be understood that alternative parameters may be used. For example, a filter (not shown) may be used to enhance accuracy of the available resolution.

Figure 3:
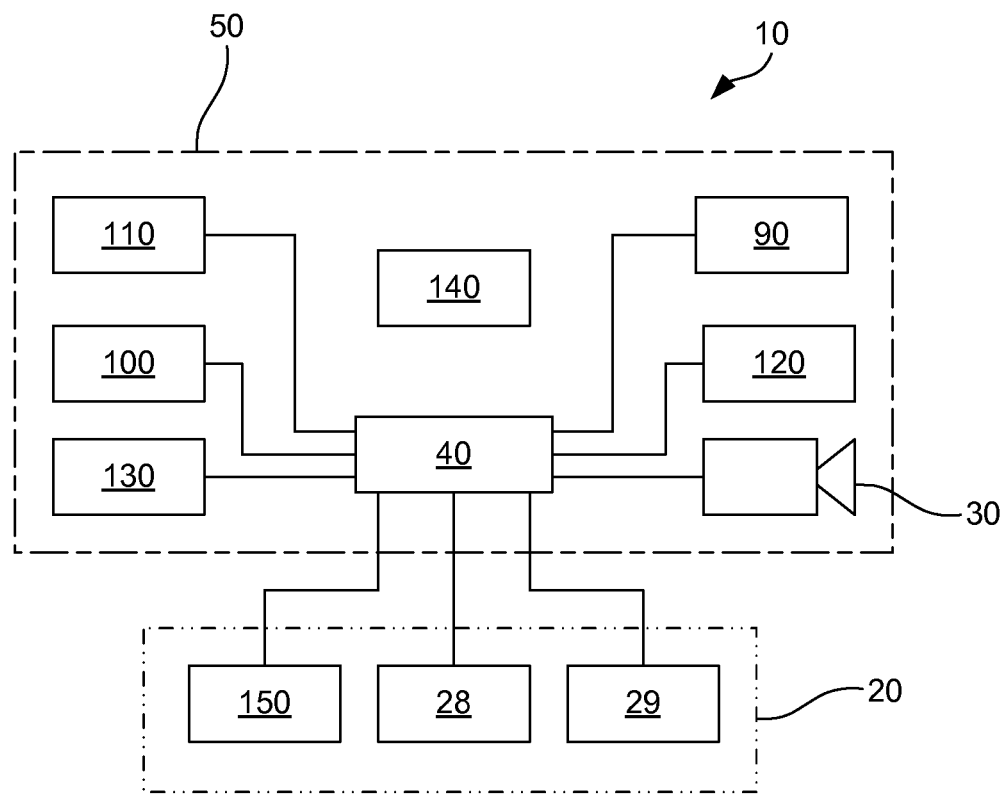
FIG. 3 shows a schematic diagram of the system of FIG. 1.

FIG. 3 shows a schematic diagram of selected components of the system 10. The system 10 has the cutting device 20, the camera 30, and the controller 40. The system 10 also has a user input 90, memory 100, RAM 110, one or more feedback modules, for example including a speaker 120 and/or a display 130, and a power supply 140. Furthermore, the system 10 has an inertial measurement unit (IMU) 150.

The memory 100 may be a non-volatile memory such as read only memory (ROM), a hard disk drive (HDD) or a solid state drive (SSD). The memory 100 stores, amongst other things, an operating system. The memory 100 may be disposed remotely. The controller 40 may be able to refer to one or more objects, such as one or more profiles, stored by the memory 100 and upload the stored one or more objects to the RAM 110.

The RAM 110 is used by the controller 40 for the temporary storage of data. The operating system may contain code which, when executed by the controller 40 in conjunction with the RAM 110, controls operation of each of the hardware components of the system 10. The controller 40 may be able to cause one or more objects, such as one or more profiles, to be stored remotely or locally by the memory 100 and/or to the RAM 110.

The power supply 140 may be a battery. Separate power supply units 140a, 140b of the power supply may separately supply the base unit 50 and the cutting device 20. Alternatively, one power supply unit may supply power to both the base unit 50 and the cutting device 20. In the present embodiments, the or each power supply unit is an in-built rechargeable battery, however it will be understood that alternative power supply means are possible, for example a power cord that connects the device to an external electricity source.

The controller 40 may take any suitable form. For instance, the controller 40 may be a microcontroller, plural controllers, a processor, or plural processors. The controller 40 may be formed of one or multiple modules.

The system 10 also comprises some form of user interface. Optionally, the system 10 includes additional controls and/or displays for adjusting some operating characteristic of the device, such as the power or cutting height, and/or informing the user about a current state of the device.

The speaker 120 is disposed in the base unit 50. Alternatively, the speaker may be on the cutting device 20 or disposed separately. In such an arrangement, the speaker will be disposed close to a user's head to enable audible signals generated by the speaker 120 to be easily heard by a user. The speaker 120 is operable in response to signals from the controller 40 to produce audible signals to the user. It will be understood that in some embodiments the speaker 120 may be omitted.

The display 130 is disposed in the base unit 50. Alternatively, the display 130 may be disposed on the cutting device 20 or disposed separately. The display 130 is operable in response to signals from the controller 40 to produce visual indicators or signals to the user. It will be understood that in some embodiments the display 130 may be omitted.

The feedback module, or one of the feedback modules, may also include a vibration motor, for example to provide tactile feedback to a user.

The user input 90 in the present embodiment includes one or more hardware keys (not shown), such as a button or a switch. The user input 90 is disposed on the base unit 50, although it will be understood that the user input 90 may be on the cutting device 20, or a combination thereof. The user input 90 is operable, for example, to enable a user to select an operational mode, to activate the system 10, and/or disable the system 10. The user input 90 may also include mechanical means to allow manual adjustment of one or more operating characteristics of the system 10.

The inertial measurement unit 150 is in the cutting device 20. In the present arrangement, the IMU 150 is received in the main body 21 of the cutting device 20. IMUs are known and so a detailed description will be omitted herein. The IMU 150 is configured to provide the readings of six axes of relative motion (translation and rotation). The IMU 150 is configured to generate information indicative of the position of the cutting device 20. The information generated by the IMU 150 is provided to the controller 40.

Although in the present and other described embodiments the position identifier is an imaging module, it will be understood that alternative means or complimentary means of generating information indicative of the position of one or more objects, in particular a part of a body to be treated and a cutting device, may be used. Examples of such a position identifier include electromagnetic field detection, microwave detection, inertial measurement, and/or ultrasonic detection. A detailed description of the alternative arrangements has been omitted. For example, the camera 30, acting as an imaging module, may be omitted and the IMU 150 may be used to generate information indicative of the position of the cutting device 20. With such an arrangement, the information indicative of the position of the cutting device 20 generated by the IMU 150 is provided to the controller 40 and/or referred to by the controller 40, and the controller 40 is configured to adjust an operating characteristic of the treating device in dependence on the information generated by the IMU 150.

In alternative embodiments, the position identifier has or includes an alternative means to generate information indicative of the position of one or more objects, in particular a part of a body to be treated and the cutting device. Such alternative means may be used instead of or in combination with one of or both of an imaging module or an IMU. For example, the position identifier may be configured to generate information indicative of the position of one or more objects based on acoustic detection, ultrasonic detection, infrared signals, detection of signal propagation time and/or angles, and/or another technique for analysing signals may be used.

Cutting device 20 may include one or more accelerometers, gyroscope or other position and/or orientation monitoring sensors to determine the position and/or orientation of cutting device 20.

In one embodiment the position identifier is configured to generate information indicative of position of the treating device 20 based on electromagnetic field detection. In such an embodiment the position identifier comprises one or more electromagnetic field detectors (not shown). The one or more electromagnetic field detectors configured detect changes in an electromagnetic field to generate information indicative of the position of the treating device relative to the part of the body to be treated based on a detected electromagnetic field.

In one embodiment one or more position indicators (not shown) which are detectable by the position identifier may be mounted to a part of the body, such as the part of the body to be treated. Such position indicators may be inactive, or may be active, for example by transmitting a signal to be detected by the position identifier. Such signals may include acoustic signals, ultrasonic signals, infrared signals, visual signals, and/or optical signals.

The position identifier may be may be mounted to the part of the body to be treated, generate information indicative of the position of the part of the body to be treated and/or the cutting device based on signals received from another part of the system, for example the cutting device 20. The position identifier may be on the cutting device. Any combination of the above described means for generating information indicative of the position of one or more objects may be used. The system 10 may use one or more different techniques to generate information indicative of the position of the treating device relative to the part of the body to be treated. The system 10 of FIG. 1 is operated by disposing the base unit 50 in a suitable location for cutting hair. That is, the base unit 50 is positioned so that the user is able to position the part of the body to be treated, for example the head, within the optical sensing zone 21. For example, the camera 30 is disposed around a height at which a user's head will be positioned during operation of the system 10. In an embodiment in which the camera 30 is separate from the base unit 50, or the base unit is omitted, the camera 30 is positioned as necessary. The hand-held cutting device 20 is held by the user.

The system 10 is actuated by a user. The controller 40 controls the driver 29 to operate the cutting unit 24 in a cutting mode. It will be understood that the cutting unit 24 may have more than one treating modes. The controller 40 controls the distance actuator 28 to determine the position of the cutting unit 24 relative to the guide face 26.

When the system is actuated, the cutting device 20 is at or between a minimum condition, in which the distance between the cutting unit 24 and the guide face 26 is at a minimum value, and a maximum condition, in which the distance between the cutting unit 24 and the guide face 26 is at a maximum value. The controller 40 initially moves into a maximum condition so that the hair is not able to be accidentally cut to a shorter length than desired.

The user uses the system 10 by holding the hand-held cutting device 20 and moving the cutting device 20 over areas of part of the body from which hair is to be cut. The guide face 26 of the cutting head 22 is placed flat against the skin and hairs being received through the guide 25 and interacting with the cutting unit 24 are cut. For example, for trimming hair in the scalp area of a user's head 81, the user positions the guide face 26 against the scalp and moves the cutting device 20 over the skin 80 from which hair to be trimmed protrudes. The user can move the cutting device 20 around the surface of the scalp. The hair being cut as the cutting device 20 is moved over the skin 80 will depend on the size and shape of the guide face 26 of the guide 25 which is disposed proximate to the skin 80 and also on the size, shape and arrangement of the cutting unit 24 of the cutting head 22.

With a conventional trimmer, the extent of the cutting action of the trimmer is difficult to predict and control and the user relies on their skill and steady hand to move the device in the appropriate manner. Furthermore, the length of the hair to be cut is dependent on a user controlling a distance between the guide face of the device and the user's skin 80 such that the trimmed length of the hair being cut, or by moving the guide into a desired position to set the cut length. This can be difficult when holding the device as any undue movement of the skin or hand may cause a mistake. Furthermore, the device and/or the hand or arm of the user may obstruct the view of the user when the device is in use and this may result in the device being moved in an undesired manner and cause inaccuracies or mistakes. Therefore, it is difficult to use such a device to achieve accurate cutting of hairs.

The invention as defined in the claims provides a system for treating a part of a body to be treated, including cutting hair, which allows for variations in the treatment, such as cutting hair, applied to a part of the body to be treated dependent on the position of the treating device relative to the part of the body to be treated. The system is operable to provide information indicative of the position of the treating device relative to the part of the body to be treated, and to change an operating characteristic of the treating device in dependence on the provided information.

The method of how the system 10 is used comprises an initial step of the user, who may be cutting hair on a part of their own body, or of another user's body, positions the cutting device 20 with respect to the part of the body on which hair is to be cut, for example the user's head. The camera 30, acting as the imaging module, is operable to generate information indicative of the position of the cutting device 20, as well as the part of the body to be treated. In the present embodiment, the camera 30 generates image data representing a scene received by the camera's sensor within the optical sensing zone 21. With such an embodiment, the camera 30 produces a depth map, for example a visual image with depth (RGB-D map) of the objects within the optical sensing zone 31.

The camera 30 is operable to generate information indicative of the part of the body to be treated based on the image produced of objects within the optical sensing zone 31. For example, the camera 30 is operable to generate information indicative of the user's head based on the image produced within the optical sensing zone 31 including the user's head. The camera 30 is configured to generate information indicative of the position and/or orientation of the user's head. To effectively determine the location of the user's head from the available map of the objects within the optical sensing zone 31, features of the user's head are identified.

In such an embodiment, the camera 30 is configured to detect a gaze direction of the user's head. That is the direction in which the head is directed relative to the camera 30. Detection of the gaze direction of the user's head based on detection of one or more objects in the image of the user's head and the treating device and, optionally, based on detection of the user's nose and/or ears in the image of the user's head and the treating device. It has been found that a user's nose and/or ears are easily locatable in an image produced of objects in the optical sensing zone 31. As a user's nose and ears protrude from the remainder of a user's head, the camera 30, it has been found that one or more of these objects are easily locatable in an image including a user's head.

Features of the user's head, for example the user's nose and/or ears, are identified by the camera 30. It has been found that the nose and ears may be detected rapidly and continuously in the depth map produced by the camera 30, acting as the imaging module, using a known detection method, for example 3D pattern matching. Although in the present arrangement the camera 30 is configured to identify the user's nose and/or ears, it will be understood that the camera 30 may be configured to detect one or more alternative features of the part of the body in the optical sensing zone 31. For example, the camera 30 may be configured to detect the shape of the user's head, eyes, lips, blemishes, scars, birthmarks and/or other facial features. Such features may be identified by the camera 30 and stored by the controller 40 in the memory 100 for reference during use of the system 10, or during future use of the system 10.

An advantage of the camera 30 being configured to detect a gaze direction of the user's head based on detection of the user's ears and nose in the image of the user's head is that generally two or more of these three features will be identifiable in the image of the part of the body irrespective of the gaze direction of the user's head. Therefore, from the overall position and orientation of these three features, it is possible to generate information indicative of the position of the position of the head across a range of different head positions relative to the camera 30. Therefore, movements of the head may be accommodated during use of the system.

The camera 30 is operable to generate information indicative of the cutting device 20, acting as a treating device. The shape of the cutting device 20 is known and may be stored, for example by the memory 100, to be referred to during operation of the camera 30. The position of the cutting device 20 is determined in a similar manner to that of the part of the body to be treated. To effectively determine the location of the cutting device 20 from the available map of the objects within the optical sensing zone 31, features of the cutting device 20 are identified. The cutting device 20 may be provided with markers (not shown) which are easily recognisable by the camera 30.

The camera 30 is configured to accommodate part of the cutting device 20 being obscured in the image produced of objects within the optical sensing zone 31. That is, the camera 30 is configured to identify two or more features of the cutting device 20 such that the camera is able to determine the location of the cutting device 20 from the available map of the objects within the optical sensing zone 31 even when one or more of the features of the cutting device 20 are occluded by another object, for example a user's hand, in the image produced of objects within the optical sensing zone 31.

Although in the above embodiment the image of the part of the body of which an image is produced corresponds to the image of the part of the body to be treated, it will be understood that the invention is not limited thereto. For example, the camera 30 may generate image data including data representative of a lower part of a user's head, and the system 10 may extrapolate this date to generate information indicative of the upper part of a user's head.

Although the camera 30 is capable of determining the position of the cutting device 20 from the available map of the objects within the optical sensing zone 31 when at least one of the features of the cutting device 20 is identifiable in the image produced of objects within the optical sensing zone 31, it has been found that the cutting device 20 may be completely occluded in the image, for example when the cutting device 20 is disposed to treat the back of the user's head and the user's gaze direction is towards the camera 30.

When the camera 30 is unable to provide information indicative of the position of the cutting device 20, or indicates that the treating device 20 is not found within the image data representing a scene received by the camera's sensor within the optical sensing zone 21, the controller 40 is configured to refer to information indicative of the position of the cutting device 20 provided by the IMU 150. The IMU 150 is disposed in the cutting device 20 and may be operable throughout use of the system 10, or only when operated by the controller 40, for example when the camera 30 is unable to detect the cutting device 20, that is out of the optical sensing zone 31 of the camera 30.

The IMU 150 is configured to generate information indicative of the position of the cutting device 20 based on the IMU's own position in the cutting device 20. The IMU 150 provides readings of 6 axes of relative motion—translation and rotation.

The controller 40 may be configured to calibrate the IMU 150 based on information generated by the camera 30 when the cutting device 20 is within the optical sensing zone 31. This helps to remove positioning errors due to the readings of the IMU 150 over time.

Although in the present embodiment the controller 40 is configured to refer to information generated by the IMU 150 when the treating device is out of an optical sensing zone of the imaging module, it will be understood that the controller 40 may be configured to refer to information generated by the imaging module and the inertial navigation system module throughout use of the system 10. In an alternative embodiment, the IMU 150 may be omitted. In such an embodiment information indicative of the position of the cutting device relative to the part of the body to be treated may be determined by extrapolation of the image data representing a scene received by the camera's sensor within the optical sensing zone 21. Alternatively, the controller 40 may be configured to provide feedback to a user, for example by audio signals, to guide the user to change their gaze direction relative to the camera 30 so that the cutting device 20 is within the optical sensing zone 31, and the camera is able to generate image data representing a scene received by the camera's sensor within the optical sensing zone 21.

With information indicative of the position of the part of the body to be treated, in this case the user's head, and the cutting device 20 known, it is possible to determine the position of the cutting device 20 relative to the part of the body to be treated based on the image of a part of the body and the cutting device 20. The relative positions may be calculated based on vector subtraction. Therefore, the relative positions may be easily determined.

Although in the above described embodiment the relative positions of the cutting device 20 and the part of the user's head to be treated are determined by the camera 30, it will be understood that the information generated by the camera 30 indicative of the position of the cutting device 20 and the part of the user's head to be treated may be provided to the controller 40 or another component of the system 10, which is configured to determine the relative positions of the cutting device 20 and the part of the user's head based on the information provided.

When the user places the cutting device 20 against the user's head and moves the device over the user's head, the system 10 is able to determine the relative positions of the cutting device 20 relative to the part of the body to be treated based on the image data generated by camera 30 of the part of the body and the cutting device. The controller 40 receives data from the camera 30 and the controller 40 is configured to adjust an operating characteristic in response to the date received. In this embodiment, the operating characteristic is the distance between the cutting unit 24 and the guide face 26.

Although in the present embodiment the operating characteristic that is changed by the controller 40 is the distance between the cutting unit 24 and the guide face 26, it will be understood that other operating characteristics of the cutting device 20 may be changed. It will be appreciated that the characteristic of the device which is changed depends on the purpose and function of the device and the invention as defined in the claims and is not limited to any particular type of device for treating hair and/or skin. Therefore, the controller may be configured to alter any characteristic of the device in dependence on the information generated by the imaging module. Other operating characteristics that may be altered include adjusting the operational speed, or some other characteristic, of the treating device, which in the present embodiment is a cutting device, or adjusting one or more characteristics of the guide 25 in combination or instead of the distance between the guide face 26 and the cutting unit 24, as will be described in detail hereinafter.

The controller 40 may be configured to alter two or more operating characteristics. Such operating characteristics may be altered concurrently or independently of each other.

In some embodiments in which the controller 40 is configured to adjust two or more operating characteristics, one of the operating characteristics of the cutting device is the distance between the cutting unit 24 and the guide face 26. Adjustment of the distance between the cutting unit 24 and the guide face 26 allows for hair to be cut to a different length dependent on the position of the cutting device 20 relative to the part of the body to be treated. By altering another operating characteristic in dependence on the position of the cutting device 20 relative to the part of the body to be treated as well as the distance between the cutting unit 24 and the guide face 26 it is possible to further improve the ability of the device to provide a desired treatment, in this case hair cutting, to the user. However, it will be understood that in an alternative embodiment the distance between the cutting unit 24 and the guide face 26 is not changed.

The controller 40 is configured to refer to a reference profile of the part of the body to be treated. The reference profile may be stored in a look-up table. The reference profile may be stored by the memory 100. In such an arrangement, the controller 40 is configured to refer to the memory 100 to access the reference profile. It will be understood that the controller 40 may be configured to refer to the RAM 110 to access the reference profile. In such an arrangement the RAM 110 is configured to store the reference profile. The controller may be configured to retrieve a reference profile from the memory 100 and upload it to the RAM 110. In such an arrangement the controller 40 may be configured to select from two or more reference profiles. The reference profile provides information of a desired setting for the or each operating characteristic to be altered by the controller 40, in this case the distance between the cutting unit 24 and the guide face 26, for each position of the cutting device 20 relative to the part of the body to be treated. Such information is communicated and stored with reference to a coordinate system. One such configuration uses a polar coordinate system in which each position on the part of the body to be treated is determined by a distance from a fixed point and an angle from a fixed direction. Another configuration uses a Cartesian coordinate system. For each point a condition, such as a value, of the operating characteristic is given. Alternatively, the reference profile may define a map of the part of the user's body to be treated which is divided into predefined areas and a condition of the operating characteristic is given for each area.

Although in one arrangement every possible position may be assigned a condition of the or each operating characteristic, in an alternative embodiment a limited number of positions are assigned a condition, and the controller 40 is configured to extrapolate and interpolate the condition for other positions based on the one or more given limited number of positions. In such an arrangement, a change in the condition for a determined position may be a step change. Alternatively, the controller 40 may configure the change to be continuous and gradual. An advantage of such an approach is that an even haircut may be achieved.

The controller 40 is configured to adjust the or each operating characteristic, for example, setting for the distance between the cutting unit 24 and the guide face 26 by comparing the provided information indicative of the position of the treating device relative to the part of the body to be treated with reference information provided by the reference profile and adjusting the operating characteristic, for example the distance between the cutting unit 24 and the guide face 26 to correspond to the reference data.

The controller 40 operates the distance actuator 28 to adjust the distance between the cutting unit 24 and the guide face 26. As the cutting unit 24 is moved over the part of the body to be treated, the controller is configured to change the operating characteristic, in this embodiment the distance between the cutting unit 24 and the guide face 26, in dependence on the determined position of the cutting device 20 relative to the part of the body to be treated. It will be understood that the cutting unit 24 and guide face 26 will both have an operating zone over which treatment will be provided. That is the cutting unit 24 will have a treating zone which, when positioned over a section of the part of the body to be treated, will affect treatment, for example hair cutting, on said section. Therefore, the treating zone may overlay two or more positions having different desired conditions of the operating characteristic. To help prevent undesired treatment, such as hair from being cut too short, in such a situation the controller 40 is configured to select the condition closest to a default condition. For example, in the present embodiment the controller 40 is configured to select the greatest distance between the cutting unit 24 and the guide face 26 provided by the two or more desired conditions. The other condition or conditions will subsequently be met by repeated, but slightly different, passes of the cutting device 20 over the part of the body to be treated.

Alternative or further operating characteristic that the controller 40 may be configured to adjust in dependence on the information generated by the position identifier is an operating characteristic of the treating unit 24 itself.

Figure 5:
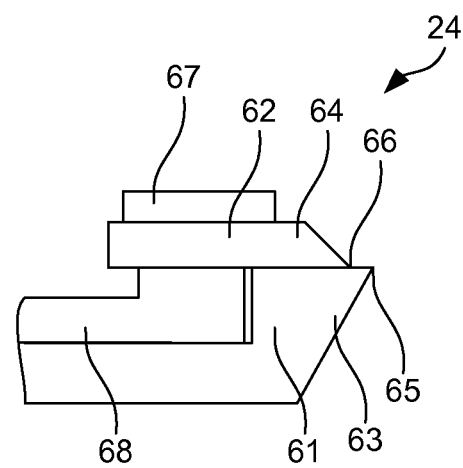
FIG. 5 shows a schematic partial cut-away side view of an embodiment of a cutting unit of the cutting device shown in FIG. 2 in an extended condition.

Referring to FIGS. 4 and 5, in one embodiment, the operating characteristic that the controller 40 is configured to adjust is the distance between the moveable edge 66 of the moveable blade 64 and the stationary edge 65 of the stationary blade 63. This adjustable distance is denoted as the tip-to-tip distance. This tip-to-tip distance of the cutting unit 24 may have an effect on the resulting length of hair cut, in particular if the guide 25 is omitted, and/or skin friendliness to the part of the body to be treated.

The cutting unit 24 comprises a driving bridge 67. The driving bridge 67 is used as a couple coupling the driver 29 to the moveable blade 64. In the present embodiment the driving bridge 67 translates the motor movement to a translational/reciprocal movement in a transverse direction to the stationary edge 65 of the stationary blade 63. The stationary blade 63 is usually designed to be thicker than the moveable blade 64.

The moveable blade 64 is actively pressed into abutment with the stationary blade 63 to receive a so-called teeth pressure. A spring (not shown) is usually used to supply said teeth pressure by resiliently biasing the moveable blade 64 against stationary blade 63. This helps ensure a good cutting performance.

As described above, it will be understood that the guide 25 generally defines the hair cut length based on the distance between the cutting unit 24 and the guide face 26. The guide 25 in other words spaces the cutting unit 24 away from the part of the body from which the hairs extend, to increase the length of the hair cut. In the present application, the term "hair cut length" denotes the length of the hairs that remain on the part of the body to be treated following treatment. However, as described above the guide 25 may be omitted, either by removal of the guide 25 or for a cutting device 20 without a guide. In such an embodiment the cutting unit 24 is exposed. Such an arrangement allows for precise trimming of hair and leads to shorter haircut lengths, which may be particularly used for outer contours of the hairline or beard.

In the present embodiment, the tip-to-tip distance of the cutting unit 24 is adjustable. The cutting unit 24 comprises an adjuster 68. The adjuster 68 is operable by the controller 40. The adjuster 68 is a linear actuator, although alternative arrangements are envisaged. The adjuster 68 is operable to move the moveable blade 64 to adjust the tip-to-tip distance. The adjuster 68 is configured to act on the moveable blade 64 to move the moveable edge 66 towards and away from the stationary edge 65.

The adjustor 68 is adapted to adjust the position of the moveable blade 64 with respect to the stationary blade 63 in an adjustment direction between a retracted position (refer to FIG. 4) and an extended condition (refer to FIG. 5). The adjustment direction is substantially perpendicular to the reciprocal motion. In the present embodiment the tip-to-tip distance is preferably adjustable between 0.3 mm and 2 mm, with a step size of 0.1 mm, although the step size may be variable. Of course, also other step sizes are technically possible, as well as a continuous, step-less adjustment.

With an embodiment in which the or one of the operating characteristics that the controller 40 is configured to adjust in dependence on the information generated by the camera 30, the controller 40 controls the driver 29 to operate the cutting unit 24 in a cutting mode. The controller 40 controls the adjuster 68 to determine the tip-to-tip distance.

When the system is actuated, the cutting device 20 is at or between a minimum condition, in which the tip-to-tip distance is at a minimum value, and a maximum condition, in which the tip-to-tip distance is at a maximum value. The controller 40 initially moves the tip-to-tip distance into a maximum condition so that the hair is not able to be accidentally cut to a shorter length than desired.

The user uses the system 10 by holding the hand-held cutting device 20 and moving the cutting device 20 over areas of part of the body from which hair is to be cut. The cutting unit 24 of the cutting head 22 is placed flat against the skin and hairs interacting with the cutting unit 24 are cut. For example, for trimming hair on a user's face, the user positions the cutting unit against the face and moves the cutting device 20 over the skin 80 from which hair to be trimmed protrudes. The user can move the cutting device 20 around the surface of the face. The hair being cut as the cutting device 20 is moved over the skin 80 will depend on the tip-to-tip distance, and also on the size, shape and arrangement of the cutting unit 24 of the cutting head 22.

In one embodiment, the or one of the operating characteristic of the cutting unit 24 that the controller 40 is configured to adjust in dependence on the information generated by the camera 30 is operation of the driver 29 in dependence on information indicative of the position of the treating device 20 relative to the part of the body to be treated generated by the camera 30. In one such an embodiment, the controller 40 is configured to determine the position of the cutting device 20 relative to the part of the body to be treated in dependence on the information generated by the camera 30 and to adjust operation of the driver 29 configured to drive the cutting unit 24. The controller 40 is configured to adjust the operating speed of the cutting unit 24 in dependence on the determined position of the cutting device 20. In one embodiment the driver 29 is an electric motor and so the controller 40 is operable to adjust the operating speed of the motor. The operating speed of the cutting unit 24 relates to the rate at which the moveable cutting blade moves in a reciprocal motion.

With such an embodiment it is possible to increase the operating speed of the cutting unit 24, for example, when it is determined that there is a high hair density as determined by the controller 40 by referring to a reference profile of hair density in dependence on the position of the cutting device 20 relative to the part of the body to be treated. Alternatively, or in addition thereto, the controller 40 may be configured to operate or cease operation of the cutting unit 24 through control of the driver 29 in dependence on a reference profile of the part of the body to be treated.

In one embodiment, the operating characteristic that the controller 40 is configured to change is the cutting unit 24 itself. In one such embodiment the cutting head 22 comprises two or more cutting units (not shown) and the controller 40 is configured to interchangeably select between the two or more cutting units in dependence on the information generated by the camera 30.

Although in the above described embodiment, the operating characteristic that the controller is configured to adjust relates to a cutting operation of the cutting device 20, it will be understood that in one or more alternative embodiments the treating unit may not be a cutting unit 24, but may be an applicator configured to dispense a substance, such as a moisturiser or a tanning cream. In such an embodiment, the controller 40 is configured to adjust the applicator to control the rate at which the substance is dispensed in dependence on the information generated by the position identifier.

In each of the above embodiments the controller 40 is described as changing one operating characteristic of the treating unit; however it will be understood that the controller may be configured to adjust two or more operating characteristics of the treating unit. Furthermore, the treating unit may have more than one operating function.

An alternative or additional operating characteristic that the controller 40 may be configured to adjust in dependence on the information generated by the position identifier is an operating characteristic of the guide 25 itself.

Figure 6:
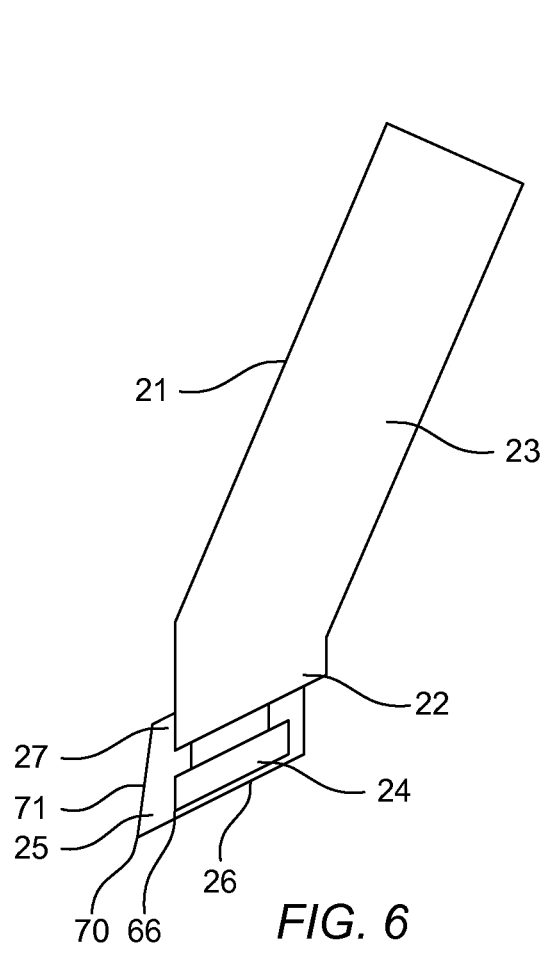
FIG. 6 shows a schematic side view of an embodiment of the cutting device shown in FIG. 2 with a guide in an extended condition.
Figure 7:
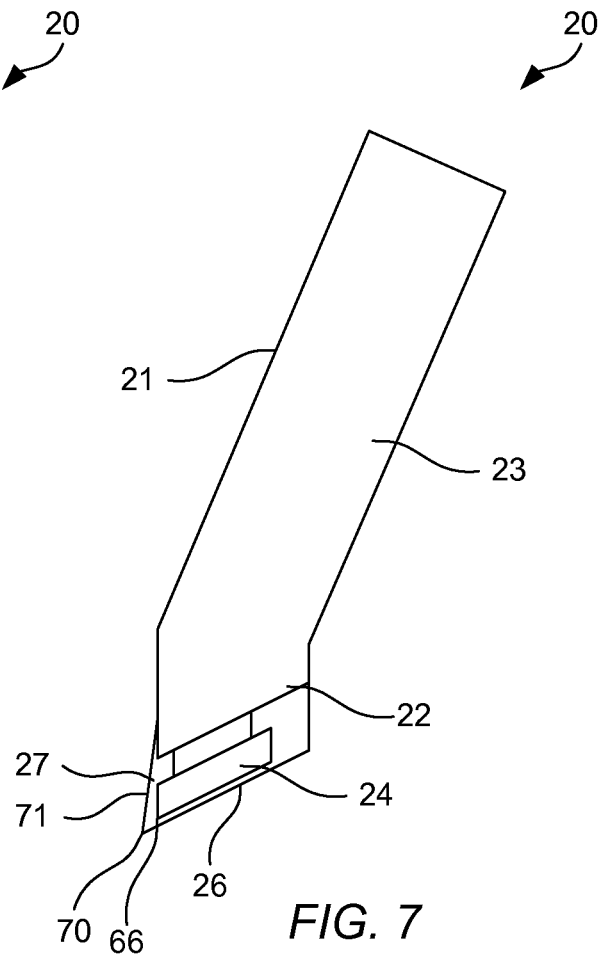
FIG. 7 shows a schematic side view of an embodiment of the cutting device shown in FIG. 2 with a guide in a retracted condition.

Referring to FIGS. 6 and 7, in one embodiment, the or one of the operating characteristic of the cutting unit 24 that the controller 40 is configured to adjust in dependence on the information generated by the camera 30 is the position of the leading edge 70 of the guide 25 relative to the moveable edge 66. That is, although in some embodiments described herein the operating characteristic that is adjustable is the distance between the guide face 26 and the cutting unit 24, in this embodiment the or one of the operating characteristics that is adjusted is the distance between the leading edge 70 of the guide 25 and the moveable edge 66 of the cutting unit 24. In particular, in one embodiment the distance between the leading edge 70 of the guide 25 and the moveable edge 66 of the cutting unit 24 independent of the distance between the guide face 26 and the cutting unit 24. The distance between the leading edge 70 and the moveable edge 66 is denoted the comb length. This distance relates to the distance that the comb teeth 27 extend from one end of the cutting unit 20.

A comb actuator (not shown) acts on the guide 25 to move the leading edge 70 of the guide 25 relative to the moveable edge 66 of the cutting unit 24. Therefore, the comb actuator is actuatable to adjust the comb length in dependence on the controller 40. The guide 25, or part of the guide 25, is moveable relative to the cutting unit 24 to alter the comb length. Therefore, the comb teeth 27 are retractable towards and extendable away from the cutting unit 24 to adjust the extent to which the comb teeth 27 extend from the one end of the cutting unit 24.

An advantage of this arrangement is that it allows the precision at which the treatment is applied to be varied. For example, when the comb teeth 27 are retracted, as shown in FIG. 7, such that the comb length is small, the precision of the cutting device 20 is increased to allow a more accurate treatment for a given cutting height of the guide due to the distance between the leading edge 70 of the guide 25 and the cutting unit 24 being reduced. Whereas, by extending the comb teeth 27, as shown in FIG. 6, an increased hair lifting effect is produced for a given cutting height of the guide 25 which helps to maximise the performance of the cutting device 20.

In one embodiment, the or one of the operating characteristic of the cutting unit 24 that the controller 40 is configured to adjust in dependence on the information generated by the camera 30 is the extent of allowable movement of the guide 25 about the cutting unit 24. That is, the extent to which the guide 25 is able to pivot about the cutting unit 24. In particular, in one embodiment the guide 25 comprises one or more connecting units (not shown) to connect the guide 25 to the cutting head 22 and/or main body 21. The connecting unit or units enable the angular position of the guide 25, and therefore the guide face 26, with respect to the cutting unit 24 to vary. It will be understood that the distance between the cutting unit 24 and the guide face 26 is maintained throughout the angular movement of the guide 25.

The or at least one of the connecting units is configured to control movement of the guide 25. That is, the or one of the connecting units is configured to control the allowable extent of angular movement of the guide 25. In the present embodiment, the controller 40 is configured to adjust the guide 25 between a locked condition, in which the angular position of the guide 25 is able to change, and a release condition, in which the angular position of the guide 25 relative to the cutting unit is changeable, in dependence on the information generated by the position identifier, for example the camera 30.

Alternatively, the controller 40 is configured to adjust the resistance to movement of the guide 25 in dependence on the information generated by the position identifier, for example the camera 30. Therefore, allowable angular movement of the guide 25 may be dampened.

By allowing angular movement of the guide 25, and controlling the extent of allowable movement, the guide 25 is able to follow the contours of the part of the body to be treated. Therefore, it is possible to manipulate the allowable movement of the guide 25 based on the indicated position of the cutting device 20 relative to the part of the body to be treated. This means that it is possible to help improve comfort of the user by varying the allowable movement of the guide 25 on different areas of the part of the body to be treated. For example, on a delicate area of the part of the body to be treated the guide 25 may be configured to be movable to allow for a gentle movement over the area, whereas on a tougher area the guide may be configured to be rigid to allow for an increased rate of movement.

An alternative or additional operating characteristic that the controller may be configured to adjust in dependence on the information generated by the position identifier is an operating characteristic of the main body 21 of the cutting device 20 itself. For example, the controller 40 may be configured to adjust the shape of the cutting device 20 in dependence on the determined relative position of the cutting device 20.

In one embodiment the flexibility of the main body 21 may be variable. For example, in one embodiment the main body 21 may be hinged and the controller 40 may be configured to control the flexibility and/or resilience of the hinge joint. Such an arrangement would allow the ergonomics of the cutting device 20 to change, and so aid the treatment.

Although in the above described embodiments the controller 40 is configured to adjust an operating characteristic of the cutting device 20, acting as a treating device, in dependence on the position of the cutting device 20 based on the information indicative of the position of the cutting device 20 relative to the part of the body to be treated generated by the position identifier, for example the camera 30, it will be understood that the controller 40 may be configured to adjust an operating characteristic of the cutting device 20 based on alternative factors based on information indicative of the position of the cutting device 20 relative to the part of the body to be treated.

In one embodiment the controller 40 may be configured to adjust an operating characteristic of the cutting device 20 based on the rate of change of position of the cutting device 20 in dependence on information indicative of the position of the cutting device 20 relative to the part of the body to be treated generated by the camera 30. In one such an embodiment, the controller 40 is configured to determine the rate at which the cutting device 20 is moved relative to the part of the body to be treated in dependence on the information generated by the camera 30. The camera 30 is able to generate information indicative of the cutting device 20 on a continuous or predefined interval basis. The camera 30 is therefore capable of providing information indicative of the path of the cutting device 20 relative to the part of the body to be treated. The controller 40 is configured to determine movement based on a comparison of the relative positions of the cutting device 20 over a predetermined time period. The controller 40 is therefore capable of determining movement of the cutting device 20 relative to the part of the body to be treated based on the information generated by the camera 30.

The controller 40 is configured to adjust operation of the driver 29 configured to drive the cutting unit 24. The controller 40 is configured to adjust the operating speed of the cutting unit 24 in dependence on the determined rate at which the treating device is moved relative to the part of the body to be treated. In one embodiment the driver 29 is an electric motor and so the controller 40 is operable to adjust operation of the driver 29 configured to drive the cutting unit 24. The operating speed of the cutting unit 24 relates to the rate at which the moveable cutting blade moves in a reciprocal motion.

With such an embodiment it is possible to increase the operating speed of the cutting unit 24, for example, when it is determined that the rate of movement of the cutting device 20 relative to the part of the body to be treated is above a predefined value. Such variations in the operating speed in dependence on the rate of movement of the cutting device may involve a step change or a gradient change, for example. In one embodiment, the controller 40 is configured to cease operation of the driver 29 when no relative movement of the cutting device 20 is determined. Such embodiment may help to minimise power consumption.

Once a full transversal of the part of the body to be treated has been completed, the user is able to move the cutting device 20 away from the part of the body to be treated. It will be understood that the cutting device 20 may be moved away from the part of the body to be treated during treatment, and the system 10 will be able to continue to operate when the cutting device 20 is moved back towards the part of the body to be treated.

Although in the above described embodiments one reference profile is used, it will be understood that the controller 40 may be configured to select from two or more reference profiles in response to a user input, or in response to information generated by the camera based on an image of a part of the body. For example, the controller 40 may be configured to select a reference profile based on a size of the head of the user as determined by the camera 30.

In the above described embodiments, the or each operating characteristic is adjusted by the controller 40 referring to a reference profile. The controller 40 is configured to refer to a reference profile of the part of the body to be treated. The reference profile may be stored in a look-up table. The reference profile may be stored by the memory 100. In such an arrangement, the controller 40 is configured to refer to the memory 100 to access the reference profile. In one embodiment, the reference profile is stored by the RAM 110.

In one embodiment, the controller 40 is configured to form a profile of the part of the body to be treated based on the one or more adjustments of the operating characteristic made in response to user input determined by the controller 40 together with the information indicative of the position of the treating device relative to the part of the body to be treated.

In such an arrangement, the operating characteristic is adjustable in response to user input. For example, a user may be able to select a manual mode which overrides the controller 40 adjusting the operating characteristic in dependence on the information generated by the position identifier. The manual mode may be selected by a user operating the user interface, for example a dedicated button. The user is then able to manually adjust the operating characteristic. In an arrangement in which the operating characteristic is the distance between the treating unit, for example, the cutting unit 24 and the guide face 26, the distance may be adjustable by the user manually acting on the cutting unit 24 or guide 25 and moving it into a desired position, or by using a user interface to manually operate the distance actuator 28 to move the cutting unit 24 into the desired position.

The controller 40 is configured to determine the adjustment made to the operating characteristic and to track the or each adjustment made by the user. That is, the controller 40 is configured to record the adjustments made and cause information indicative of the adjustments made to be stored by the RAM 110. Alternatively, the controller 40 is configured to cause the information to be stored by the memory 100.

The controller 40 is configured to modify the reference profile based on the information indicative of the or each adjustment made to the operating characteristic. In such an embodiment, the controller 40 is configured to determine the or each adjustment made in response to user input for one or more positions of the cutting unit relative to the part of the body, based on information generated by the camera 30. The controller 40 is configured to modify the reference profile with this data to form a new reference profile. The modified reference profile is then caused to be stored in the memory 100 or RAM 110 by the controller 40 for future reference by the controller 40.

In one embodiment the controller 40 is configured to form the reference profile. In such an embodiment, the controller 40 is configured to determine the condition of the operating characteristic, for example the distance between the cutting unit 24 and the guide face 26, in dependence on the position of the cutting unit 24 relative to the part of the body to be treated based on information generated by the camera 30. That is, the controller 40 is configured to track changes to the operating characteristic made in response to user input and to record the data to form a reference profile. The reference profile may be in the form of a look-up table or other recording configuration. The reference profile is then caused to be stored in the memory 100 or RAM 110 by the controller 40 for future reference by the controller 40.

Although in the above described embodiments the tracked changes to the operating characteristic are dependent on the controller 40 determining changes to the operating characteristic, for example the distance between the cutting unit 24 and the guide face 26, made in response to user input, it will be understood that in an alternative embodiment the controller 40 is configured to track desired changes in response to a user input, for example a user inputting a desired change to the operating characteristic without the change being effected. The controller 40 is then configured to form a modified or new reference profile based on the tracked desired changes. The reference profile may be in the form of a look-up table or other recording configuration. The new or reference profile is then caused to be stored in the memory 100 or RAM 110 by the controller 40 for future reference by the controller 40.

In an alternative embodiment not shown in the Figures, the controller does not automatically adjust the one or more operating characteristics in dependence on the information generated by the imaging module, but rather informs the user of the cutting device via one or more feedback modules, for example the speaker 120 and/or display 130. For example, while the cutting device is in use the controller will alter an operating characteristic of the feedback unit to inform the user in dependence on the information generated by the imaging module so that they can take the appropriate action. The feedback module may provide an acoustic signal, in the form of an audible sound such as a beeping sound. Alternatively, the feedback module may provide tactile feedback in the form of vibrations that are felt by the user via the handle of the device. Alternatively, the feedback module may provide an optical signal, such as flashing light or other optical indicator. It will be appreciated that the feedback module may also provide more than one of the above mentioned signals in dependence on the information generated by the imaging module.

Although in the above described embodiments the camera is a depth camera, it will be understood that alternative imaging modules may be used. For example, alternative vision systems acting as an imaging module may be used. Such an alternative vision system may include a non-range camera, for example using an object reconstruction technique, or stereo vision, temporal analysis of video to reconstruct range data and detect the head position and cutting device position, analysis of thermal camera images, analysis of data from ultrasonic sensors, and/or analysis of data from capacitive sensors.

Although in the above described embodiments, the system and method are described as a system for cutting hair on a part of a body and a method of cutting hair on a part of a body, it will be understood that the invention is not limited thereto. For example, the system and method may be used as an alternative treatment of a part of the body to be treated. The operating characteristic that is altered in dependence on the information generated by the imaging module will depend on the purpose and function of the device.

It will be appreciated that the system and/or method as defined in the claims may be used for any method of treating hair or skin. For example, the device may be an epilator, shaver, trimmer, exfoliator, microdermabrasion device, laser hair cutting device, moisturiser, intense pulsed light based device, or any other powered device which interacts with the hair and/or skin of a user. The device may apply a substance such as colouring agent, shampoo, medical substance or any other substance to the hair or skin of the user. Possible alternative uses include systems incorporating one or more non-invasive or invasive treatments such as a tooth brush, a shaver, alternative types of hair removal other than cutting, skin cleaning, skin tanning, and/or skin rejuvenation. In such embodiments, the treating of a part of body may include application of light, application of a lotion or other fluids, and/or puncturing.

The device may have two or more treating units. In such an arrangement the controller may be configured to adjust an operating characteristic of the different treating units in different ways. For example, in an arrangement with two cutting units the cutting height of one of the cutting units may be altered independently of the other of the cutting units. Therefore, it will be appreciated there are many ways in which the controller is able to adjust an operating characteristic of a device having multiple treating units.

It will be appreciated that the term "comprising" does not exclude other units or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A hair cutting system for hair cut treating a part of a body said system comprising:
   a hand-held-hair cutting treating device comprising:
      a cutting unit comprising:
         a stationary treating element comprising a stationary blade with a stationary blade edge; and
         a moveable treating element comprising a moveable blade with a blade edge, said blade edge of said moveable blade being arranged parallel to the stationary blade edge, wherein the moveable blade is moveable in a reciprocal direction to the stationary blade; and
      a guide, reciprocally moveable with regard to the cutting unit, comprising:
         a guide face comprising:
            comb teeth, extendable from one end of the cutting unit, defining a leading edge of the guide, wherein the guide face is configured to:
               contact said part of the body; and
               space said cutting unit from said contacted part of the body;
      a driver configured to:
         drive the moveable blade in a direction traverse to the reciprocal direction of the moveable blade; and
   a position identifier comprising:
      an imaging module configured to:
         generate information indicative of a position of the hair cutting treating device relative to the part of the body to be treated; and
   a controller configured to;
      receive said information generated by the position identifier;
      adjust at least one operating characteristic of the treating device in dependence on the information generated by the position indicating device; and
      adjust operation of the treating device in dependence on the adjusted at least one operating characteristic.

2. The hair cutting system according to claim 1, wherein the at least one operating characteristic of the hair cutting treating device is adjustable in response to a user input, and
the controller is configured to:
   determine one or more adjustments of the at least one operating characteristic made in response to the user input; and
   form a profile of the part of the body to be treated based on the one or more adjustments of the operating characteristic and information indicative of the position of the hair cutting treating device relative to the part of the body to be treated.

3. The hair cutting system according to claim 1, wherein the controller is configured to:
   modify a reference profile of the part of the body to be treated in response to a user input; and
   generate a new reference profile based on the modification of the reference profile.

4. The hair cutting system according to claim 3, wherein the controller is configured to:
   form the reference profile based on the user input together with the information indicative of the position of the treating device relative to the part of the body to be treated.

5. The hair cutting system according to claim 1, wherein the controller is configured to:
   change a distance between the stationary blade edge and the movable blade edge in the reciprocal direction.

6. The hair cutting system according to claim 1, wherein the controller is configured to:
   adjust a distance between the stationary blade edge and the moveable blade edge in the reciprocal direction.

7. The hair cutting system according to claim 1, wherein the controller is configured to:
   adjust a distance between the cutting unit and the guide face.

8. The hair cutting system according to claim 1,
wherein the guide face is configured to be moveable to follow contours of the part of the body to be treated, and
wherein the controller is configured to:
adjust an extent of movement of the guide face about the treating unit.

9. The system according to claim 8, wherein said extent of movement of the guide face is a linear movement.

10. The hair cutting system according to claim 7, wherein the controller is configured to:
adjust an extent to which the comb teeth extend from the one end of the cutting unit.

11. The hair cutting system according to claim 1,
wherein the controller is configured to:
adjust a shape of the treating device in dependence on the determined position of the treating device.

12. A hair cutting system comprising:
a cutting device comprising:
a first blade including a first blade edge,
a second blade including a second blade edge, said second blade configured to be one of: transversely movable and linearly movable, with respect to the first blade edge; and
a guide comprising:
a plurality of teeth projecting linearly forward of said first blade edge, said guide being removable attachable to said cutting device;
a driver configure to:
drive the second blade traverse to the first blade;
a means to position said second blade edge linearly from said first blade edge; and
a position identifier comprising:
a position indicating device comprising:
an imaging module configured to:
generate an image of said cutting device and an object, wherein said image contains therein positions of said cutting device and said object; and
provide the determined positions to a controller, wherein said controller is configured to:
receive the determined positions of the cutting device and the position of the object;
determine a relationship between the cutting device and the object; and
alter a condition of the cutting device based on the determined relationship, wherein said altered condition changing an operation of the cutting device with respect to cutting hair on said object.

13. The hair cutting system of claim 12, wherein said altered condition of the cutting device is one of: an altered linear distance between the second blade and the first blade edge, an altered speed of a transverse movement of the second blade edge with respect to the first blade edge, and an altered shape of said cutting device.

14. The hair cutting system of claim 12, wherein said altered condition of the cutting device comprises an altered distance between said guide teeth and said first blade edge.

15. The hair cutting system of claim 12, wherein said altered condition of the cutting device is based on said relationship between the cutting device and the object with respect to a reference profile of said object.

* * * * *